(12) United States Patent
Botto et al.

(10) Patent No.: US 10,137,077 B2
(45) Date of Patent: Nov. 27, 2018

(54) **COSMETIC USE OF *ARTEMIA SALINA* EXTRACT TO PROTECT SKIN FROM THERMAL STRESS**

(71) Applicant: ISP INVESTMENTS, LLC, Wilmington, DE (US)

(72) Inventors: Jean-Marie Botto, Garbejaïre (FR); Valère Busuttil, Nice (FR); Karine Cucumel, Opio (FR); Neil Astles, Nice (FR); Nouha Domloge, Valbonne (FR)

(73) Assignee: ISP Investments, LLC, Wilmington, DE (US)

( * ) Notice: Subject to any disclaimer, the term of this patent is extended or adjusted under 35 U.S.C. 154(b) by 280 days.

(21) Appl. No.: 15/107,000

(22) PCT Filed: Mar. 6, 2015

(86) PCT No.: PCT/FR2015/000050
§ 371 (c)(1),
(2) Date: Jun. 21, 2016

(87) PCT Pub. No.: WO2015/107286
PCT Pub. Date: Jul. 23, 2015

(65) Prior Publication Data
US 2017/0042802 A1    Feb. 16, 2017

(30) Foreign Application Priority Data

Jan. 8, 2014 (FR) .................................. 14 50132

(51) Int. Cl.
| | | |
|---|---|---|
| *A61K 36/00* | (2006.01) | |
| *A61K 8/98* | (2006.01) | |
| *A61Q 17/00* | (2006.01) | |
| *A61K 8/97* | (2017.01) | |
| *A61Q 19/00* | (2006.01) | |
| *A61K 35/612* | (2015.01) | |

(52) U.S. Cl.
CPC ............... *A61K 8/987* (2013.01); *A61K 8/97* (2013.01); *A61K 35/612* (2013.01); *A61Q 17/00* (2013.01); *A61Q 19/00* (2013.01); *A61K 2800/591* (2013.01)

(58) Field of Classification Search
USPC ........................................................ 424/725
See application file for complete search history.

(56) References Cited

U.S. PATENT DOCUMENTS

2005/0129779 A1    6/2005   Dal Farra et al.

FOREIGN PATENT DOCUMENTS

| CN | 103251652 A | 8/2013 |
|---|---|---|
| FR | 2810241 A1 | 12/2001 |
| FR | 2817748 A1 * | 6/2002 |
| FR | 2834887 A1 | 7/2003 |
| FR | 2835743 A1 | 8/2003 |
| RU | 2429865 C1 | 9/2011 |
| WO | 99/38483 | 8/1999 |

OTHER PUBLICATIONS

PCT, International Search Report, International Application No. PCT/FR2015/000050, dated Jul. 10, 2015.
Fujita, Jun, "Cold Shock Response in Mammalian Cells," J. Mol. Microbiol. Biotechnol., vol. 1, No. 2, pp. 243-255 (1999).
Marino, Frank et al., "Whole Body Cooling by Immersion in Water at Moderate Temperatures," Journal of Science and Medicine in Sport, 1 (2), pp. 72-81 (1998).
Sonna, Larry A. et al., "*Molecular Biology of Thermoregulation* Invited Review: Effects of heat and cold stress on mammalian gene expression," J. Appl. Physiol. 92, pp. 1725-1742 (2002).

* cited by examiner

*Primary Examiner* — Michael V Meller
(74) *Attorney, Agent, or Firm* — FisherBroyles, LLP; Susan M. Oiler

(57) ABSTRACT

Methods of protecting skin from damage due to cold thermal stress are disclosed. The methods include topically applying a composition that includes an *Artemia salina* extract from rehydrated *Artemia salina* cysts to skin at risk of damage from thermal stress, particularly from cold thermal stress or repeated temperature variations. The composition includes a physiologically acceptable medium for delivery of the *Artemia salina* extract.

6 Claims, 2 Drawing Sheets

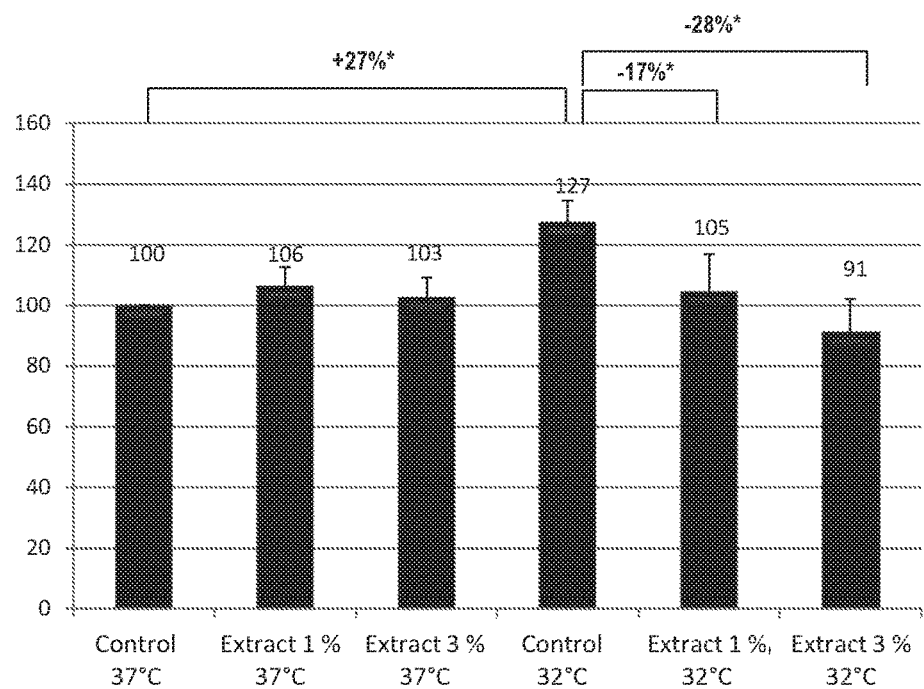
Figure 1 : Expression of CIRBP following cold thermal stress in cells treated or not treated by Artemia extract

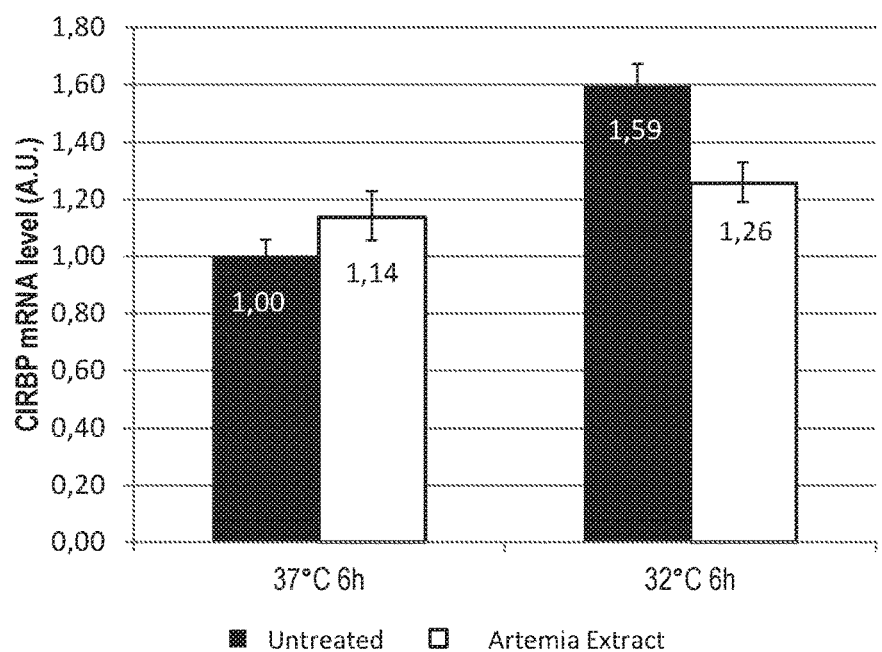
Figure 2 : Evaluation of CIRBP mRNA after cold thermal stress in cells treated or not treated by Artelia extract

US 10,137,077 B2

COSMETIC USE OF *ARTEMIA SALINA* EXTRACT TO PROTECT SKIN FROM THERMAL STRESS

FIELD OF THE INVENTION

The present invention is situated in the cosmetic field, and more specifically in the field of protective cosmetic skincare. The invention relates to the cosmetic use of *Artemia salina* extract to protect the skin from damage caused by thermal stress, particularly from cold thermal stress or repeated temperature variations.

Another object of the invention is a method of cosmetic care comprising the topical application, on at least one portion of the skin of the body or face, of an *Artemia salina* extract, in a composition comprising a physiologically acceptable medium, to obtain a protective effect, and more specifically to protect the skin from damage due to thermal stress.

BACKGROUND OF THE INVENTION

The main function of the epidermis is to ensure a protective barrier between the external environment and the body. Skin, in direct contact with the external environment, is exposed to many changes in environmental conditions. Depending on the nature and extent of the changes, they can cause damage responsible for physical, chemical or biological stress. The main stresses are thermal stress, exposure to free radicals of oxygen, ultraviolet and infrared radiation, heavy metals, osmotic shock and pressure shock and also pathological conditions such as fever, inflammation, viral infection, etc.

Thermal stress is defined as stress affecting the body's optimal functioning and which exceeds the body's physiological thermoregulation mechanisms. Thermal stress is produced following a decrease (cold thermal stress) or an increase (hot thermal stress) in temperature, of environmental or internal origin. A deviation of a few degrees from this optimal temperature can have significant consequences.

Thermal shock is defined as stress caused by a sudden and significant temperature variation (temperature change of at least 10° C.).

Skin can be exposed to thermal stress in many physiological or accidental situations. The average skin temperature can be estimated as a constant value that is about 33° C. in optimal functioning, and can quickly change depending on exposure to the environment, for example it falls to 27° C. after immersion in a 24° C.-bath (Marino and Booth, 1998) and can rise beyond 37° C. following sun exposure.

Cold thermal stress can include deep hypothermia, in which the temperature of tissues and organs falls below 25° C. (such as exposure to extreme cold temperatures or else in certain medical techniques to protect the organs and tissues from hypoxia), and moderate hypothermia (temperature of between 25° C. and 35° C.) as in, for example, repeated exposure to air conditioning when moving between inside rooms and the outside every day in summer and winter, or else bathing.

The skin is frequently subjected to moderate cold thermal stress followed by successive warmings. The following are among the cellular physiological effects of exposure to cold (Fujita et al.):

Increased protein denaturation and disaggregation
Slowdown in progression through the cell cycle, the G1 phase generally being the most sensitive
Inhibition of transcription and translation, which leads to a general reduction in protein synthesis
Disruption in elements of the cellular cytoskeleton
Changes in membrane permeability which leads to increased cytosolic Na+ and H+ ions.

In addition, repeated skin exposure to repeated temperature variations can cause harmful effects on cell phenotype or else on the structure and lipid compositions of cellular membranes, thus altering the barrier function of the skin and leading to irritation, dryness or else cracking. These effects due to temperature variations and cold thermal stress accelerate the aging process of the skin.

Resistance to thermal stress is enabled by the establishment of a specific cellular response. In the case of cold thermal stress, the cell establishes a protection system by inducing the transcription of a specific gene family that results in the synthesis and intracellular accumulation of cold shock proteins or "CSP," these being different from heat shock proteins or "HSP."

Among CSPs, Cold-inducible RNA-binding protein, or CIRBP, is a protein coded, in humans, by the CIRBP gene. These proteins are expressed constitutively as well as after exposure to cold. CIRBP plays a critical role in controlling cellular response to a variety of cellular stresses, including short wavelength ultraviolet light, hypoxia and hypothermia. Its expression rapidly and significantly increases during moderate hypothermia (Fujita et al., J. Mol. Microbiol. Biotechnol., 1999; Larry et al, J. Appl. Physiol., 2002) among the other roles of CIRBP:

Inhibition of RNA degradation
Increase in the transcription of specific target genes via elements from the promoter region of these genes,
Alternative splicing of pre-mRNA The special properties of CIRBPs make them interesting biological markers of the body's reaction to temperature shocks.

Extracts of *Artemia salina* are already used in cosmetics. For example, document FR 2 817 748 describes an *Artemia salina* extract for preventing skin aging due to UV damage, document FR 2 835 743 describes an *Artemia salina* extract for limiting the side effects of retinoids and application WO 1999038483 describes a cosmetic product based on *Artemia salina* extracts for the regeneration and stimulation of skin cells.

However, to date, no one has established a connection between an *Artemia salina* extract and the protection of skin from damage due to thermal stress.

The inventors have demonstrated that the application of an effective quantity of an *Artemia salina* extract enables cells to be protected from thermal stress that can cause skin damage, particularly cold thermal stress or repeated temperature variations.

The invention and resulting advantages will be better understood upon reading the description.

DISCLOSURE OF THE INVENTION

The present invention relates to the cosmetic and/or dermatological use of an *Artemia salina* extract to protect the skin from damage due to thermal stress.

According to the invention, the term "skin" includes all of the keratinous appendages present on the surface of the body, particularly body hair, eyelashes, eyebrows, nails and hair.

Thus, "protect the skin from damage due to temperature variations" is understood to mean, in the sense of the present invention, an *Artemia salina* extract used to reduce or prevent skin damage and irritation, caused by repeated variations in temperature or by cold thermal stress. Repetitive skin damage is considered unsightly and is often associated with accelerated skin aging.

The invention also relates to the cosmetic and/or dermatological use of an *Artemia salina* extract to protect the skin from damage due to thermal stress.

The invention also relates to the cosmetic and/or dermatological use of an *Artemia salina* extract to protect the skin from damage due to sudden and/or repeated temperature variations.

The invention also relates to the cosmetic and/or dermatological use of an *Artemia salina* extract to maintain a physiological level of CIRBP in skin cells exposed to cold thermal stress.

In fact, *Artemia salina* is a small crustacean that lives in brackish water. When environmental conditions become difficult (dehydration, increased mineral content), the *Artemia* encapsulates and enters into a dormancy phase in which it can remain for several years. When conditions become favorable again, the *Artemia* rehydrates and resumes its development cycle smoothly.

Due to adaptation to its hypermineralized biotope, *Artemia salina* managed to develop important adaptation skills: It synthesizes GP4G (diguanosine tetraphosphate), a precursor molecule of ATP, GTP and a G protein activator. It has cells specialized in regulating osmolarity, a corollary of the good hydromineral balance of plankton.

In a particular embodiment, *Artemia* extract contains between 120 and 195 mg/liter of diguanosine tetraphosphate, preferably at least 150 mg/liter of diguanosine tetraphosphate.

In what follows, the terms "active agent" and "*Artemia salina* extract" will be used interchangeably.

"Topical application" is understood to refer to the act of applying or spreading the active agent according to the invention, or a composition containing the agent, to or on the surface of the skin or a mucous membrane.

"Physiologically acceptable" is understood to mean that the active agent according to the invention, or a composition containing it, is appropriate for entering in contact with the skin or mucous membrane without causing toxicity or intolerance reactions.

"Damage due to thermal stress" is understood to mean exposure to cold, resulting in weakening, drying, irritating or else cracking the area of skin that had been damaged.

In particular embodiments, the *Artemia* extract according to the invention can be diluted in one or more physiologically suitable solvents, such as water, glycerol, ethanol, propanediol, butylene glycol, dipropylene glycol, ethoxylated diglycol or propoxylated diglycol, cyclic polyols or any mixture of these solvents.

Another object of the present invention is a method of cosmetic care comprising the topical application, on at least one portion of the skin of the body or face, of an *Artemia salina* extract, in a composition comprising a physiologically acceptable medium, to protect the skin from damage due to thermal stress.

The present invention also relates to a method of cosmetic care comprising the topical application, on at least one portion of the skin of the body or face, of an *Artemia salina* extract, in a composition comprising a physiologically acceptable medium, to protect the skin from damage due to repeated temperature variations and/or to cold thermal stress.

Advantageously, the *Artemia* extract is present at a concentration of between 0.0001% and 20% of the total weight of the composition, preferentially at a concentration of between 0.01% and 10% of the total weight of the composition, and still more preferentially at a concentration of between 0.05% and 5% of the total weight of the composition, in a physiologically acceptable medium.

According to another advantageous embodiment of the invention, the active agent may be encapsulated or included in a cosmetic carrier such as liposomes or any other microcapsule utilized in the cosmetic field or adsorbed on powdery organic polymers, mineral supports such as talcs and bentonites.

The compositions for implementing the invention may be, in particular, present in the form of an aqueous, hydroalcohol or oily solution; an oil in water emulsion, water in oil emulsion or multiple emulsions; They may also be present in the form of suspensions or else powders, suitable for application on the skin, mucous membranes, lips and/or hair.

These compositions may be more or less fluid and have the appearance of a cream, lotion, milk, serum, pomade, gel, paste or foam. They may also be present in solid form, such as a stick, or may be applied on the skin in aerosol form.

These compositions may also comprise any additive commonly utilized in the contemplated field of application as well as the adjuvants necessary for their formulation, such as solvents, thickeners, diluents, antioxidants, colorants, sunscreens, self-tanning agents, pigments, fillers, preservatives, fragrances, odor absorbers, cosmetic or pharmaceutical active ingredients, essential oils, vitamins, essential fatty acids, surface active agents, film-forming polymers, etc.

In all cases, the person skilled in the art will make sure that these adjuvants as well as their proportions are chosen so as to not harm the desired advantageous properties of the composition according to the invention. These adjuvants may, for example, correspond to 0.01 to 20% of the total weight of the composition. When the composition of the invention is an emulsion, the fatty phase may represent from 5 to 80% by weight and preferably from 5 to 50% by weight with relation to the total weight of the composition. The emulsifiers and co-emulsifiers utilized in the composition will be chosen from among those conventionally utilized in the field under consideration. For example, they may be utilized in a proportion going from 0.3 to 30% by weight with relation to the total weight of the composition.

Advantageously, the composition usable for achieving the invention may comprise, in addition to the active agent according to the invention, at least one other active agent presenting effects that are similar and/or complementary to those of the invention. According to the invention, this active agent will be defined as an "additional active agent."

For example, the additional active agent(s) can be chosen from among: Anti-aging, firming, clarifying, moisturizing, draining agents, promoting microcirculation, pharmaceutical agents, exfoliants, desquaming agents, stimulating the extracellular matrix, activating energy metabolism, antibacterial, antifungal, soothing, anti-radical, anti-UV, anti-acne, anti-inflammatory, anesthetic agents, procuring a sensation of heat, procuring a sensation of coolness, slimming agents.

Such additional agents can be chosen from the groups comprising:
vitamin A and particularly retinoic acid, retinol, retinol proprionate, retinol palmitate,
vitamin B3 and more specifically niacinamide, tocopherol nicotinate,
vitamin B5, vitamin B6, vitamin B12, panthenol, vitamin C, particularly ascorbic acid, ascorbyl glucoside, ascorbyl tetrapalmitate, magnesium and sodium ascorbyl phosphate, vitamins E, F, H, K, PP, coenzyme Q10, metalloproteinase inhibitors, or TIMP activators, DHEA, its precursors and its derivatives, amino acids such as arginine, ornithine, hydroxyproline, hydroxyproline dipalmitate, palmitoyl glycine, hydroxylysine, methionine and its derivatives, N-acyl amino acid compounds, natural or synthetic peptides, including di-, tri-, tetra-, penta- and hexapeptides and their lipophilic derivatives, isomers, and complexes with other species such as a metal ion (e.g. copper, zinc, manganese, magnesium, and others). For example peptides commercially known by the names MATRIXYL®, ARGIRELINE®, COLLAXYL™, PEPTIDE VINCI 02™, CHRONOGEN™, LAMINIXYL IS™, PEPTIDE Q10™, plant peptide extracts such as extracts of soy, spelt, grapevine, rapeseed, linseed, rice, corn, peas, yeast extracts, dehydroacetic acid (DHA), synthetic or natural phystosterols, salicylic acid and its derivatives, alpha- and beta-hydroxy acids, silanols, amino sugars, glucosamine, D-glucosamine, N-acetyl-glucosamine, N-acetyl-D-glucosamine, mannosamine, N-acetyl mannosamine, galactosamine, N-acetyl galactosamine, extracts of polyphenols, isoflavones, flavonoids, such as grape extracts, pine extracts, olive extracts, lipids such as ceramides or phospholipids, oils of animal origin, such as squalene or squalane; vegetable oils, such as sweet almond oil, coconut, castor, jojoba, olive, rapeseed, peanut, sunflower, wheat germ, corn germ, soy, cotton, alfalfa, poppy seed, winter squash, evening primrose, millet, barley, rye, safflower, *passiflora*, hazelnut, palm, apricot kernel, avocado, *calendula* oil; ethoxylated vegetable oils, shea butter, All UV filters and sunscreens, cyclic AMP and its derivatives, activator agents of the enzyme adenylate cyclase and inhibiting agents of the enzyme phosphodiesterase, extract of *centella asiatica*, asiaticoside and asiatic acid, xanthine methyl, theine, caffeine and its derivatives, theophylline, theobromine, forskolin, esculin and esculoside, ACE inhibitors, peptide Val-Trp, neuropeptide Y inhibitors, enkephalin, *gingko biloba* extract, *dioscorea* extract, rutin, yerba mate extract, guarana extract, oligosaccharides, polysaccharides, carnitine, ivy extract, *fucus* extract, hydrolyzed extract of *Prunella vulgaris*, hydrolyzed extract of *Celosia cristata*, extract of *Anogeissus leiocarpus*, extract of *Manihot utilissima* leaves, palmitoylcarnitine, carnosine, taurine, elder extract, seaweed extracts such as *Palmaria Palmata* extract, synthetic peptide of sequence Arg-Gly-Ser-NH2, sold by the name ATPeptide™.

The usable composition according to the invention will be applied by any appropriate route, notably oral, or topical external, and the formulation of compositions will be adapted by the person skilled in the art.

Advantageously, the composition according to the invention is present in a form that is suitable for topical application. These compositions therefore must contain a physiologically acceptable medium, i.e., a medium compatible with the skin and epithelial appendages, and must cover all cosmetic forms.

Of course, it is obvious that the invention is aimed at mammals in general, and more particularly at human beings.

Particular embodiments of this cosmetic treatment method also result from the previous description. Other advantages and characteristics of the invention will more clearly appear upon reading the examples given for illustrative and non-limiting purposes.

FIG. 1: Expression of CIRBP after cold thermal stress in cells treated or not treated by *Artemia* extract.

FIG. 2: Evaluation of CIRBP mRNA after cold thermal stress in cells treated or not treated by *Artemia* extract.

EXAMPLE 1: PREPARATION OF AN *ARTEMIA SALINA* EXTRACT 50 grams of *Artemia salina* cysts are rehydrated for 30 minutes to 6 hours in 1 liter of distilled water at a temperature ranging from 30° C. to 75° C., in a suitable medium, mainly constituted of water, and at a pH of between 4 and 7. These cysts are then ground. The extract thus obtained is centrifuged and filtered. The extract is then sterilized by sterilizing filtration and heated to 65° C.

The extract is then processed to conform to cosmetic requirements (color, fragrance, appearance, sterility, etc.).

An assay by high-performance liquid chromatography (HPLC) is then carried out to confirm a diguanosine tetraphosphate content of over 150 mg/liter.

EXAMPLE 2: EXPRESSION OF CIRBP AFTER COLD THERMAL STRESS IN CELLS TREATED OR NOT TREATED By *Artemia* Extract According to the Invention The purpose of this study is to determine the effect of a pretreatment with *Artemia salina* extract on keratinocytes subjected to hypothermic stress. In particular, the CIRBP (Cold-Inducible RNA Binding Protein) was assayed by Western blot on keratinocytes subjected to moderate hypothermia (32° C.), with or without pretreatment by *Artemia salina* extract according to example 1.

Protocol:

Normal human keratinocytes (NHK) from skin are treated by adding an *Artemia salina* extract according to example 1, at 1% and 3%, to their growth medium. This application is repeated once a day for 48 hours. At the same time, NHK cultures are maintained without treatment, so as to constitute an untreated control. This culture occurs at 37° C.

Then, the pretreated or not pretreated NHK cultures are subjected to hypothermic stress by placing them at 32° C. for 6 hours. After this incubation, the NHK are lysed in order to analyze CIRBP expression by Western blot. This conventional Immunoblotting technique comprises the following steps: saturation of the transfer membrane by a 1×TBS/5% milk solution for 1 hour, incubation with the primary antibody CIRBP (Novusbio), at 4° C. for the night and then incubation with the secondary antibody coupled to peroxidase (Santa Cruz) for 1 hour at ambient temperature. Luminescence is revealed by adding the substrate (SuperSignal West Dura Extended Duration Substrate, Thermo Scientific) using a camera (Chemi-Imager system, Alpha Innotech Corporation).

Results:

The results, with reference to FIG. 1, show a 27% increase in CIRBP expression when the cells are incubated at 32° C. for 6 hours, compared to the control at 37° C. and in agreement with bibliographic data.

When the cells have been pretreated by *Artemia salina* extract at 1% according to example 1, the CIRBP level decreases significantly at 32° C., by 17%, compared to the control at 32° C. When the cells have been pretreated by *Artemia salina* extract at 3% according to example 1, the CIRBP level decreases significantly at 32° C., by 28%, compared to the control at 32° C.

Conclusion:

A decrease in CIRBP expression is observed in cells pretreated by *Artemia salina* extract at 1% or 3% according to example 1, and subjected to cold thermal stress, compared to untreated control cells.

EXAMPLE 3: EVALUATION OF CIRBP MRNA FOLLOWING COLD THERMAL STRESS

The purpose of this study is to determine if CIRBP mRNA are modulated by treatment with an *Artemia salina* extract obtained according to example 1, prior to moderate hypothermic stress (32° C.). The CIRBP mRNA level was evaluated by quantitative PCR (Q-PCR).

Protocol:

Normal human keratinocytes (NHK) are treated by an *Artemia salina* extract at 1% in the growth medium. At the same time, NHK cultures are maintained without treatment, so as to constitute an untreated control. This culture occurs at 37° C. Then, the treated and untreated cultures are placed at 32° C. for 6 hours.

After this incubation, total RNA are extracted with the RNeasy mini kit (QIAGEN, 74104) and reverse transcribed with the High Capacity cDNA reverse-transcription kit containing RNase inhibitors (Applied Biosystems, 4368814). Quantitative PCR is carried out using the Step One Plus thermocycler (Applied Biosystems). The primers and probes of the target CIRBP and of the endogenous control 18S are from Taqman Expression Assays (Applied Biosystems, Hs99999901_s1 for 18S and CIRBP: Hs00989762_g1), diluted in sterile water from Master Mix (Applied Biosystems).

Results:

The results, as presented in FIG. 2, demonstrated a significant increase of 59% in the expression of CIRBP mRNA in untreated keratinocytes subjected to moderate hypothermia (32° C.), compared to the control at 37° C.

In the case where keratinocytes were treated by *Artemia salina* extract at 1% prior to exposure to hypothermic stress, their CIRBP mRNA level increased by 12% compared to keratinocytes pretreated by the extract at 37° C. and the CIRBP mRNA level decreased by 33%, compared to the untreated control keratinocytes at 32° C.

Conclusion:

A lower level of CIRBP mRNA is observed in keratinocytes pretreated by *Artemia salina* extract according to example 1, and subjected to hypothermia, compared to untreated control cells.

EXAMPLE 4: EFFECT OF THE EXTRACT FROM EXAMPLE 1 ON TRANS EPIDERMAL WATER LOSS (TEWL)

Objective:

The study evaluates the efficacy of *Artemia salina* extract obtained according to example 1 on the protection of skin exposed to thermal stress, particularly on trans epidermal water loss (TEWL) during hot/cold stress. Trans epidermal water loss (TEWL) is a parameter that indirectly reflects the skin's permeability and barrier function (Toby Mathias et al., 1981). Hot/cold stress mimics differences in temperature between the inside and the outside in both summer and winter.

Protocol:

The study was conducted on 19 volunteers, aged 21 to 52 years, including 9 in a "mature" group (aged 48 to 57) and 10 in a "young" group (aged between 21 and 34 years).

Depending on the volunteers, the nature of the skin was normal or dry, without skin pathology, and of phototype 2 to 4.

The test was carried out double blind, versus 1% *Artemia salina* extract according to example 1 and lasted 3 weeks.

The *Artemia salina* extract from example 1 and a placebo were applied 2 times per day, morning and night, at product concentration on an identical area of each thigh.

The amount of product applied was 2 mg/cm$^2$.

Thermal stress process: First of all a heating pad (WELLYS® electric heating pad) was applied to the thigh for 10 min. Immediately afterwards, an ice pack was applied for 10 min. (FirstIce® (EZY WRAP) ice pack).

Trans epidermal water loss (TEWL) was evaluated using a Dermalab® evaporimeter (Cortex Technology). The measurement is expressed in g/m$^2$/h and is interrupted when the standard deviation is 0.1 or after 60 seconds. The measurement is taken under controlled temperature and humidity conditions (21° C.±1 and 50%±5).

Preparation Method:
1) Baseline measurements,
2) Application of products,
3) Measurements on Day 0 to Day 21 before the stress and Day 21 after the stress.

To analyze the results, we observed the time to obtain a plateau of the TEWL measurements curve. This time corresponds to the time that it takes the skin to recover, i.e., return to its baseline state, after thermal stress. We call this time the "recovery time." Next we statistically compare this recovery time for the sides treated with the extract according to example 1 and the sides treated with the placebo.

After the stress, TEWL measurements are taken every 2 min.

Result:

We note that the curve plateau is reached faster for the areas treated with *Artemia* extract than for the regions treated with the placebo.

The recovery time is significantly 27% faster on average for the areas treated with *Artemia* extract than for the regions treated with the placebo.

Conclusion:

The TEWL values return to normal faster following cold-hot thermal stress on the areas treated with the *Artemia salina* extract according to example 1 compared to the placebo. This result shows that *Artemia salina* extract helps the skin recover more rapidly following hot/cold thermal stress.

EXAMPLE 5: PREPARATION OF COMPOSITIONS

1 Protective Cream

| Ingredients (Brand Name | INCI) | | Weight percent | Supplier |
|---|---|---|---|
| Phase A | | | |
| Deionized Water | Water/aqua | Qsp 100 | |
| Phase B | | | |
| RAPITHIX ™ A-100 polymer | Sodium Polyacrylate | 0.50 | Ashland |
| Phase C | | | |
| AMPHISOL ™ K | Potassium Cetyl Phosphate | 0.50 | DSM |
| Phase D | | | |
| ROKONSAL ™/LIQUAPAR ™ MEP preservative | Phenoxyethanol (and) Methylparaben (and) Ethylparaben (and) Propylparaben | 1.00 | Ashland |
| Phase E | | | |
| CERASYNT ™ 945 ester | Glyceryl Stearate & Laureth-23 | 2.50 | Ashland |
| NACOL ™ 16-98 | Cetyl Alcohol | 2.00 | Sasol/IMCD |
| Cerabeil White | Cera Alba | 2.00 | Baerlocher |
| ANTARON ™ V-220F | VP/Eicosene Copolymer | 1.00 | Ashland |
| ESCALOL ™ 517 UV filter | Butyl Methoxydibenzoylmethane (Avobenzone) | 3.00 | Ashland |
| ESCALOL ™ 587 UV filter | Ethylhexyl Salicylate | 5.00 | Ashland |
| ESCALOL ™ 597 UV filter | Octocrylene | 7.00 | Ashland |
| CERAPHYL ™ 368 ester | Ethylhexyl Palmitate | 5.00 | Ashland |
| XP PMX ™-0245 | Cyclopentasiloxane | 5.00 | Dow Corning/Univar |
| Phase F | | | |
| OPTIPHEN ™ MIT Ultra preservative | Phenylpropanol & Propylene glycol & Methylisothiazolinone | 0.30 | Ashland |
| Phase G | | | |
| Amidon de Maïs MST | Zea Mays Starch | 2.00 | Sensient |
| Phase H | | | |
| Pf. Evasion | Parfum/fragrance | 0.50 | Technicoflor |
| GP4G SP ™ biofunctional | Water (and) Artemia Extract | 1.00 | Ashland |
| Total | | 100.00 | |

Preparation Method
1. Homogenize phase A in the main tank
2. Sprinkle over phase B and homogenize for 10 minutes, and then start to heat to 50° C. and mix well for 30 minutes
3. Decrease the temperature and add phase C. Mix well to homogenize
4. In a beaker set aside, prepare phase D, heat to 55-60° C. until homogenized and decrease the temperature
5. Add the elements from phase E one by one into the main tank, mixing well between each addition
6. Add phase D (at ambient temperature) to the main vessel and mix until homogenized
7. At 25° C., add phase F and mix well
8. Premix phase G before adding it to the main tank
9. Add the elements from phase H one by one, mixing well between each addition.
10. Stop at 25° C.

2 Moisturizing Cream for Men

| Ingredients (Brand Name | INCI) | | Weight percent | Supplier |
|---|---|---|---|
| Phase A | | | |
| Deionized Water | Water/Aqua | Qsp 100 / | |
| Na4EDTA | Tetrasodium EDTA | 0.05 | Fisher |
| Phase B | | | |
| POLYSURF ™ 67 CS polymer | Cetyl Hydroxyethylcellulose | 0.10 | Ashland |
| Phase C | | | |
| ULTRATHIX ™ P-100 Polymer | Acrylic Acid/VP Crosspolymer | 0.80 | Ashland |

-continued

| Ingredients (Brand Name | INCI) | | Weight percent | Supplier |
|---|---|---|---|
| Phase D | | | |
| REFINED SHEA BUTTER ™ | *Butyrospermum Parkii* (Shea) Butter | 1.10 | Ashland |
| ORCHID COMPLEX OS ™ ester | Caprylic/Capric Triglyceride (and) *Cymbidium Grandiflorum* Flower Extract | 3.50 | Ashland |
| Phase E | | | |
| LUBRAJEL ™ Oil Free Hydrogel | Glycerin (and) Glyceryl Acrylate/Acrylic Acid | 3.00 | Ashland |
| LUBRAJEL ™ II XD Free Hydrogel | Glycerin (and) Glyceryl Polyacrylate | 2.00 | Ashland |
| BELSIL ™ DM 5 | Dimethicone | 4.00 | Wacker |
| UNICERT ™ Yellow 08005-J (sol. 0.1%) | Water/aqua (and) CI 19140 (Yellow 5) | 0.09 | Sensient |
| UNICERT ™ Blue 05601-J (sol. 0.1%) | Water/aqua (and) CI 42090 (Blue 1) | 0.21 | Sensient |
| Optiphen ™ preservative | Phenoxyethanol (and) Caprylyl Glycol | 0.50 | Ashland |
| Phase F | | | |
| Surfin 96 | Alcohol | 7.00 | Deulep |
| Phase G | | | |
| Deionized Water | Water/Aqua | 1.50 | / |
| Sodium Hydroxide | Sodium Hydroxide | 0.08 | Fisher |
| Phase H | | | |
| Parfum Desiro Blue | Parfum/Fragrance (Limonene (and) Linalool (and) Citronellol (and) Hydroxyisohexyl 3-cyclohexene carboxaldehyde) | 0.25 | Luzi/Speciatec |
| GP4G SP ™ biofunctional | Water/aqua (and) *Artemia* extract | 1.00 | Ashland |
| AQUA-OSMOLINE ™ biofunctional | Water (and) Glycerin (and) *Ceratonia Siliqua* (Carob) Seed Extract | 1.00 | Ashland |
| Total | | 100.00 | |

Preparation Method
1. Homogenize phase A in the main tank
2. Sprinkle over phase B and homogenize for 10 minutes until homogenized
3. In a beaker set aside, prepare phase C, homogenize until homogenized. Sprinkle in phase D and mix well until homogenized
4. At 25° C., add phase C+D to the main vessel and mix until homogenized
5. At 25° C., add phase E to the main vessel and mix until homogenized
6. At 25° C., add phase C to the main vessel and mix until homogenized
7. Stop at 25° C.

3 Eye Balm

| Ingredients (Brand Name | INCI) | | Weight percent | Supplier |
|---|---|---|---|
| Phase A | | | |
| Deionized Water | Water/Aqua | Qsp 100 | / |
| Na4EDTA | Tetrasodium EDTA | 0.01 | Fisher |
| Phase B | | | |
| RAPITHIX ™ A-100 | Sodium Polyacrylate | 1.8 | Ashland |
| Phase C | | | |
| CEGESOFT ™ VP | Vegetable oil (and) Hydrogenated vegetable oil (and) Candelilla Wax | 3.00 | Cognis |
| SI-TEC ™ GF 3096 | Dimethicone (and) Dimethiconol | 10.00 | Ashland |
| Phase D | | | |
| DC 9701 Cosmetic Powder | Dimethicone/Vinyl Dimethicone Crosspolymer (and) Silica | 1.00 | Dow Corning |
| Phase E | | | |
| OPTIPHEN ™ preservative | Phenoxyethanol (and) Caprylyl Glycol | 0.50 | Ashland |
| ZEMEA ™ | Propanediol | 5.00 | Dupont Tate & Lyle |
| Phase F | | | |
| UNICERT ™ Blue 05601-J (sol. 0.1%) | Water/aqua (and) CI 42090 (FD&C Blue No. 1) | 0.20 | Sensient |
| GP4G SP ™ biofunctional | Water/aqua (and) *Artemia* extract | 1.00 | Ashland |
| Total | | 100.00 | |

Preparation Method
1. Add water to the main tank and start heating to 80° C.
2. Sprinkle in phase B at 60° C. and mix well until homogenized.
3. At 80° C., add phase C, mix well and add phase D
4. Add the ingredients from phase E into a beaker set aside and heat to 75-80° C.
5. At 80° C., add phase E to the main tank and mix well. The emulsion should be homogenized.
6. Start cooling
7. At 65° C., add phase F and mix well
8. Cool to 30° C. and add phase G and then phase H, mixing well between each phase until homogenized
9. Stop at 25° C.

The invention claimed is:

1. A method of cosmetic care to protect the skin of a human or animal from damage due to cold thermal stress, the method comprising:
    topically applying at least once or twice daily for at least two days, on at least one portion of the skin of the body or face of the human or animal which has been subjected to cold thermal stress, a composition comprising a physiologically acceptable medium and an *Artemia salina* extract obtained from rehydrated *Artemia salina* cysts,
    wherein the *Artemia salina* extract is present in the composition at a concentration of about 0.0001% to about 20% of the total weight of the composition, and the cells of the at least one portion of skin of the body or face of the human or animal maintain a physiological level of cold-inducible RNA-binding protein.

2. The cosmetic care method according to claim 1, wherein said *Artemia salina* extract is diluted in one or more physiologically suitable solvents, chosen from among water, glycerol, ethanol, propanediol, butylene glycol, dipropylene glycol, ethoxylated diglycol or propoxylated diglycol, cyclic polyols or any mixture of these solvents.

3. The cosmetic care method according to claim 1, wherein said *Artemia salina* extract is present at a concentration of about 0.05% to about 5% of the total weight of the composition.

4. The cosmetic care method according to claim 1, wherein the composition further comprises at least one additional active agent chosen from among vitamin A, retinoic acid, retinol, vitamin B3, vitamin B5, vitamin B6, vitamin B12, vitamin C, vitamin E, vitamin F, vitamin H, vitamin K, vitamin PP, coenzyme Q10, metalloproteinase inhibitors, amino acids, carnitine, carnosine, taurine, natural or synthetic peptides, vegetable peptide extracts, yeast extracts, natural or synthetic phystosterols, salicylic acid, oligosaccharides, polysaccharides, amino sugars, polyphenols, flavonoids, lipids, phospholipids, cyclic AMP and its derivatives, activator agents of the enzyme adenylate cyclase and inhibiting agents of the enzyme phosphodiesterase, theine, theophylline, theobromine, forskolin, esculin, ACE inhibitors, *dioscorea* extract, guarana extract, ivy extract, *fucus* extract, seaweed extracts such as Palmaria *Palmata* extract, hydrolyzed extract of *Prunella vulgaris* or elder extract.

5. The cosmetic care method according to claim 1, wherein said *Artemia salina* extract is present at a concentration of about 0.01% to about 10% of the total weight of the composition.

6. The cosmetic care method according to claim 1, wherein topically applying the composition comprises applying about 2 mg/cm$^2$.

* * * * *